(12) United States Patent
Puskas

(10) Patent No.: US 10,327,736 B1
(45) Date of Patent: Jun. 25, 2019

(54) ULTRASOUND TRANSDUCER ARRAYS AND ASSOCIATED SYSTEMS AND METHODS

(71) Applicant: William L. Puskas, New London, NH (US)

(72) Inventor: William L. Puskas, New London, NH (US)

( * ) Notice: Subject to any disclaimer, the term of this patent is extended or adjusted under 35 U.S.C. 154(b) by 0 days.

(21) Appl. No.: 15/955,543

(22) Filed: Apr. 17, 2018

(51) Int. Cl.
*B06B 1/02* (2006.01)
*B06B 1/06* (2006.01)
*A61B 8/00* (2006.01)

(52) U.S. Cl.
CPC .......... *A61B 8/4494* (2013.01); *B06B 1/0207* (2013.01); *B06B 1/0622* (2013.01); *B06B 1/0662* (2013.01)

(58) Field of Classification Search
CPC .............................. A61B 8/4494; B06B 1/0622
USPC .......... 310/316.01, 317, 325, 334, 321, 337, 310/319, 320, 322, 369, 323.12; 600/459, 600/467; 73/625, 626; 134/34, 1.3
See application file for complete search history.

(56) References Cited

U.S. PATENT DOCUMENTS

| | | | | | |
|---|---|---|---|---|---|
| 6,002,195 | A * | 12/1999 | Puskas | ...................... | B01J 19/10 310/312 |
| 6,181,052 | B1 * | 1/2001 | Puskas | ...................... | B01J 19/10 310/325 |
| 6,313,565 | B1 * | 11/2001 | Puskas | .................. | B06B 1/0269 310/316.01 |
| 7,449,004 | B2 * | 11/2008 | Yamada | ............. | A61B 17/2202 600/104 |

* cited by examiner

*Primary Examiner* — Thomas M Dougherty
*Assistant Examiner* — Karen B Addison
(74) *Attorney, Agent, or Firm* — Lathrop Gage LLP

(57) ABSTRACT

An ultrasound transducer array for coupling sonic energy into a liquid includes a plurality of transducer pairs, where each transducer pair includes an inverted ultrasound transducer and a non-inverted ultrasound transducer electrically coupled in series. A method for coupling sonic energy into a liquid includes (a) driving a first transducer pair with a first electrical signal, where the first transducer pair includes a first inverted ultrasound transducer and a first non-inverted ultrasound transducer electrically coupled in series and (b) driving a second transducer pair with the first electrical signal, where the second transducer pair is electrically coupled in parallel with the first transducer pair, and where the second transducer pair includes a second inverted ultrasound transducer and a second non-inverted ultrasound transducer electrically coupled in series.

20 Claims, 16 Drawing Sheets

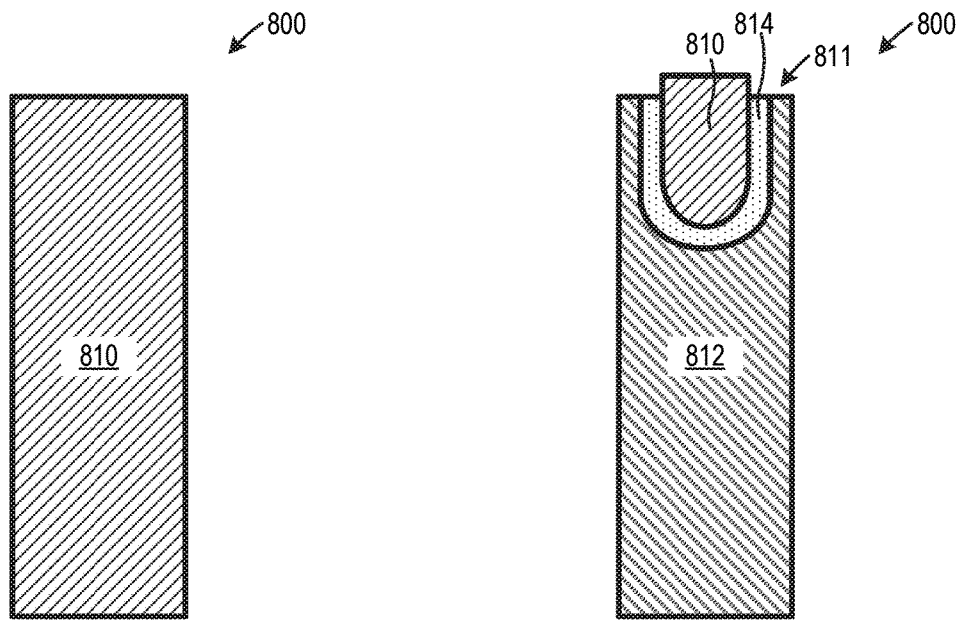
FIG. 8                    FIG. 9
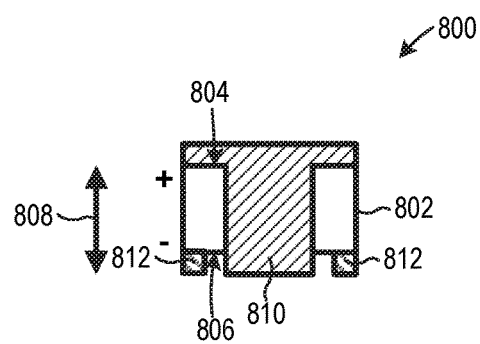
FIG. 10

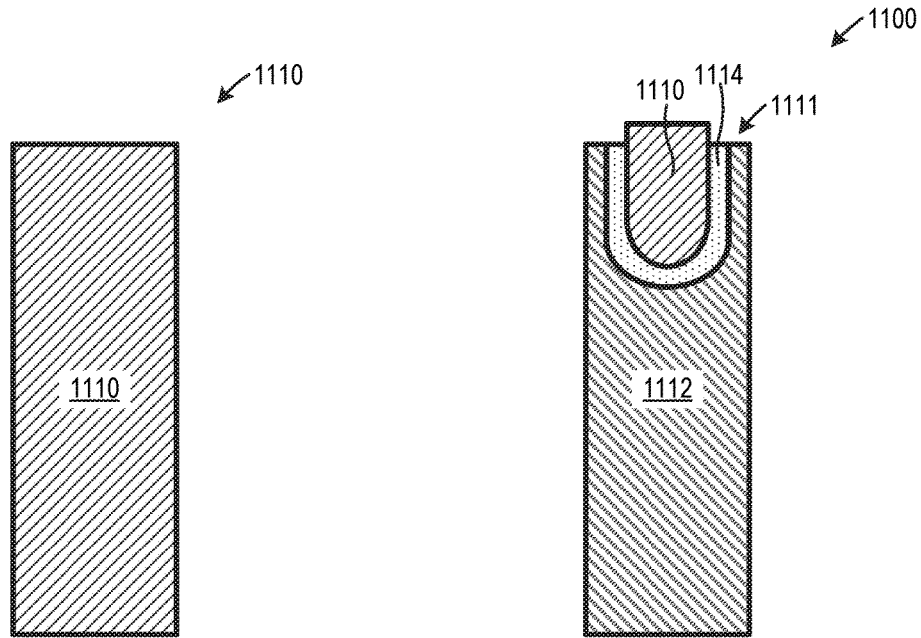
FIG. 11  FIG. 12
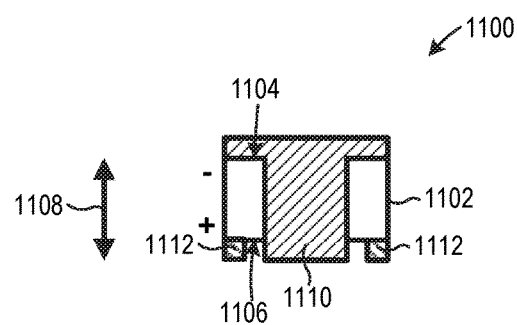
FIG. 13

ULTRASOUND TRANSDUCER ARRAYS AND ASSOCIATED SYSTEMS AND METHODS

BACKGROUND

Energy in the form of sonic, ultrasonic, or megasonic waves may be transmitted into liquid media for a variety of purposes. For example, an object may be cleaned or processed by immersing the object in liquid and subsequently transferring ultrasound to the liquid. As another example, liquids can be emulsified, homogenized, pasteurized, sterilized, or mixed by applying ultrasound thereto. As yet another example, organisms in a liquid can be inactivated by applying ultrasound to the liquid.

Ultrasound systems are commonly used to generate sound waves for transmitting into a liquid. Conventional ultrasound systems include an ultrasound transducer array constructed by bonding piezoelectric elements or Langevin assemblies to a tank for containing a liquid. A signal generator electrically drives the transducer array, and constituent transducers of the transducer array spatially oscillate in response thereto, thereby generating sound waves which are transmitted to the liquid. The sound waves and the liquid interact to produce cavitation, which may result in a cleaning effect and/or a processing effect.

FIG. 1 is an electrical schematic illustrating a conventional ultrasound system 100 including an ultrasound transducer array 102, a signal generator 104, and wiring 106. Ultrasound transducer array 102 includes a plurality of ultrasound transducers 108 affixed to a radiating element (not shown), and each ultrasound transducer 108 includes one or more piezoelectric elements. Signal generator 104 includes an alternating current (AC) electrical power source 110 electrically coupled in series with a resonant inductor 112. Wiring 106 electrically couples each ultrasound transducer 108 in parallel with signal generator 104. Signal generator 104 generates an electrical signal to drive ultrasound transducers 108.

BRIEF DESCRIPTION OF THE DRAWINGS

FIG. 8 is a top plan view of another piezoelectric element, according to an embodiment.

FIG. 9 is a bottom plan view of the FIG. 8 piezoelectric element.

FIG. 10 is an elevation view of an end of the FIG. 8 piezoelectric element.

FIG. 11 is a top plan view of yet another piezoelectric element, according to an embodiment.

FIG. 12 is a bottom plan view of the FIG. 11 piezoelectric element.

FIG. 13 is an elevation view of an end of the FIG. 11 piezoelectric element.

DEFINITIONS

In this document, the following definitions apply:

The term "megasonic" refers sound energy with a fundamental frequency from about 350 kilohertz (kHz) to about 15 megahertz (MHz).

The term "ultrasonic" refers to sound energy with a fundamental frequency from about 18 kHz to about 350 kHz.

Each of the terms "sonic," "sound waves," and "sound energy" refers to the complete range of sound waves, including audible, ultrasonic, and megasonic frequencies, ranging from about 0.2 kHz to about 15 MHz.

The term "ultrasound" refers to both ultrasonic and megasonic sound energy, with a fundamental frequency ranging from about 18 kHz to about 15 MHz.

DETAILED DESCRIPTION OF THE EMBODIMENTS

Figure 1:
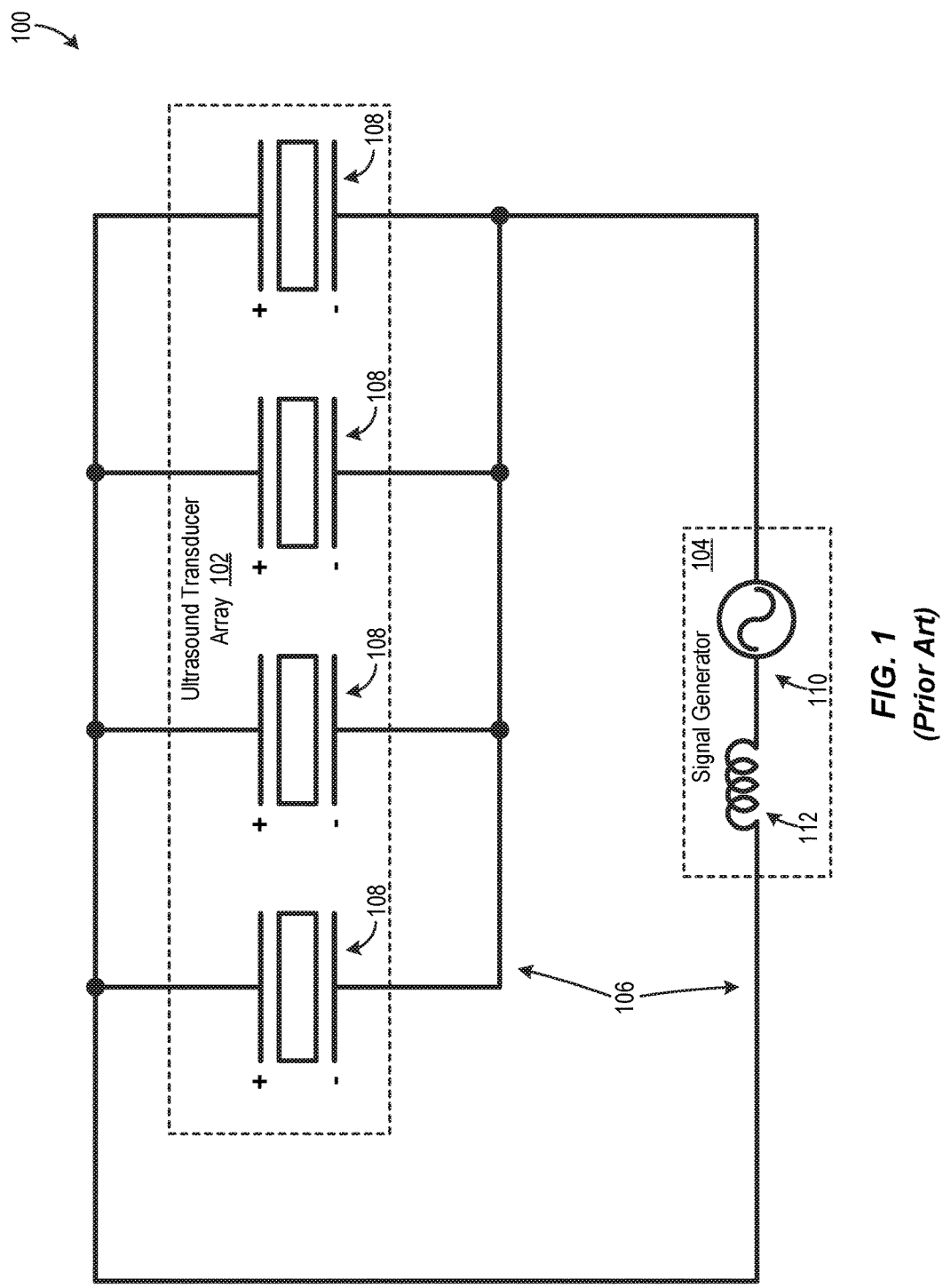
FIG. 1 is an electrical schematic illustrating a conventional ultrasound system.

Ultrasound transducers exhibit capacitances due to the capacitive nature of their constituent elements, and conventional ultrasound transducer arrays therefore have relatively large capacitance values. For example, conventional ultrasound transducer array 102 (FIG. 1) has a capacitance value approximately equal to the sum of the respective capacitance values of each ultrasound transducer 108 in the array.

Applicant has determined that the relatively large capacitance values of conventional ultrasound transducer arrays can be problematic. In particular, resonant frequency ($f_o$) of an ultrasound transducer array is characterized by EQN. 1 below, where L is inductance of an electrical circuit including the ultrasound transducer array, and C is capacitance of the electrical circuit including the ultrasound transducer array. Capacitance C is typically dominated by capacitance of the ultrasound transducer array, while inductance L is typically attributed primarily to inductance of a resonant inductor electrically coupled to the circuit, e.g., resonant inductor 112 of FIG. 1.

$$f_o = \frac{1}{2\pi\sqrt{LC}} \quad \text{(EQN. 1)}$$

As evident from EQN. 1, small values of inductance L and/or capacitance C are required to achieve a high resonant frequency $f_o$. Consequently, if the ultrasound transducer array has a large capacitance value, the inductance L value must be small to obtain a high resonant frequency $f_o$. Such small inductance values are often impractical to achieve. For example, parasitic inductance of an electrical circuit including the ultrasound transducer array will often be greater that the inductance value L required to achieve a high resonant frequency $f_o$ at a large value of capacitance C. Therefore, it can be difficult or even impossible to achieve high resonant frequencies with conventional ultrasound transducer arrays.

Furthermore, capacitance of an ultrasound transducer array is typically significantly temperature-dependent. As a result, capacitance C will vary with temperature, thereby causing resonant frequency $f_o$ to vary with temperature, because resonant frequency is a function of capacitance C, as evident from EQN. 1 above. Temperature-induced variation of resonant frequency $f_o$ is ordinarily undesirable, and such variation is more difficult to control with increasing values of capacitance C.

Applicant has developed new ultrasound transducer arrays for coupling sonic energy into a liquid. These new ultrasound transducer arrays promote low capacitance, thereby helping mitigate the problems discussed above. The new ultrasound transducer arrays include a plurality of transducer pairs, where each transducer pair includes an inverted ultrasound transducer and a non-inverted ultrasound transducer electrically coupled in series. In each transducer pair, the respective polarities of one or more piezoelectric elements of the inverted ultrasound transducer are reversed with respect to the polarities of corresponding piezoelectric elements of the non-inverted ultrasound transducer. The plurality of transducer pairs are electrically coupled in parallel such that like polarities of piezoelectric elements are connected together. The series connection of the inverted and non-inverted ultrasound transducers in each transducer pair causes the transducer pair to have a net capacitance value that is less than the respective capacitance value of each ultrasound transducer of the pair. For example, if the inverted and non-inverted ultrasound transducers have the same capacitance value, the net capacitance of the transducer pair will be half of the respective capacitance value of each ultrasound transducer of the pair. As a result, the new ultrasound transducer arrays have significantly lower capacitance values than conventional ultrasound transducer arrays with like number of ultrasound transducers of similar capacitance.

The relatively low capacitance values of the new ultrasound transducer arrays may advantageously enable the new ultrasound transducer arrays to operate at a higher resonant frequency than conventional ultrasound transducer arrays. Additionally, the relatively low capacitance values of the new ultrasound transducer arrays can help reduce temperature-induced resonant frequency variation, relative to conventional ultrasound transducer arrays.

Figure 2:
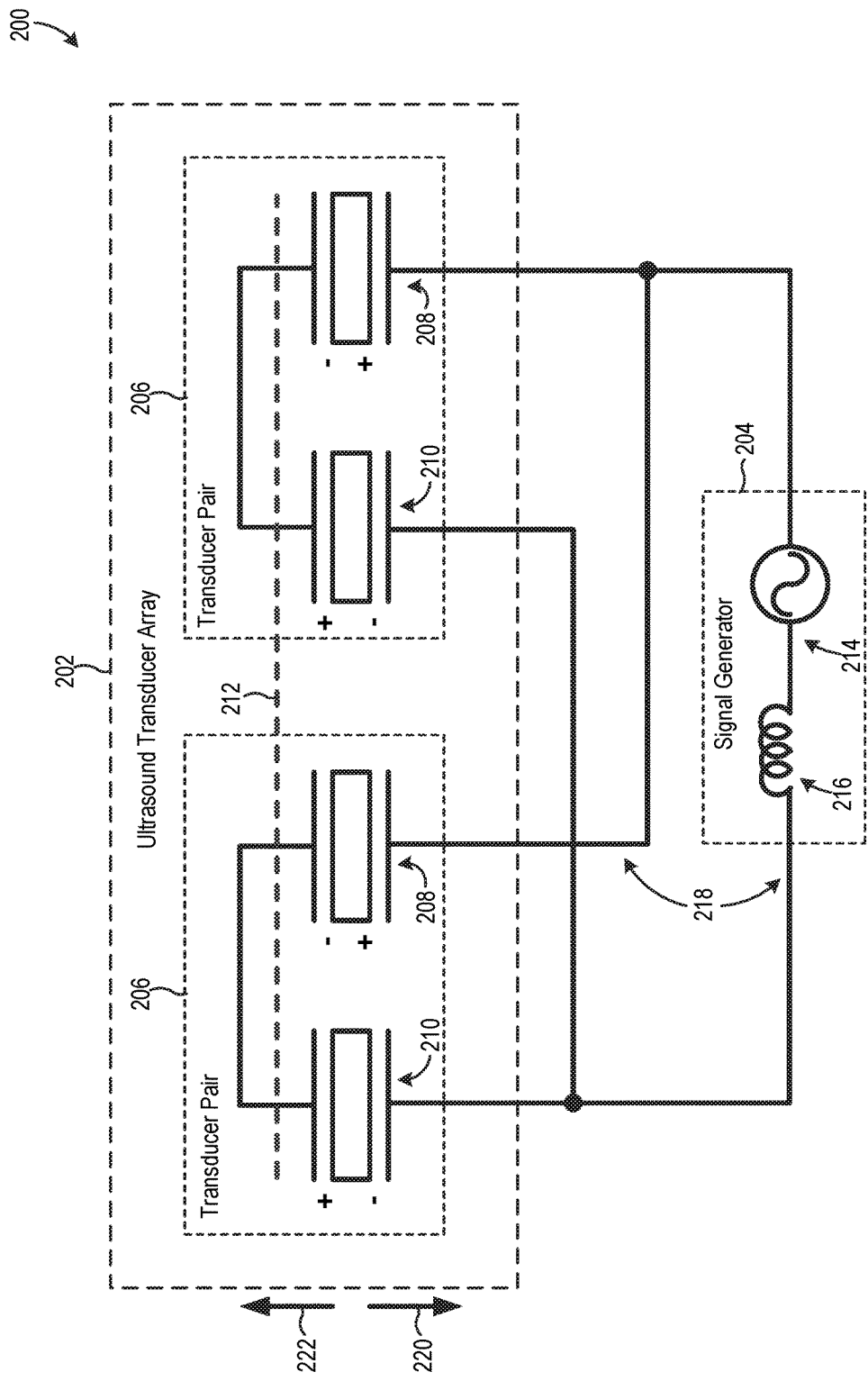
FIG. 2 is an electrical schematic illustrating an ultrasound system including an ultrasound transducer array which promotes low capacitance, according to an embodiment.

FIG. 2 is an electrical schematic illustrating an ultrasound system 200 including an ultrasound transducer array 202 electrically coupled to a signal generator 204. Ultrasound transducer array 202 is one embodiment of the new ultrasound transducer arrays developed by Applicant, and ultrasound transducer array 202 includes a plurality of transducer pairs 206 electrically coupled in parallel such that like polarities of piezoelectric elements are connected together to form the parallel configuration, i.e., positive poles from transducer pairs 206 are connected together, and negative poles from transducer pairs 206 are connected together. Although ultrasound transducer array 202 is depicted as including two transducer pairs 206, ultrasound transducer array 202 could include additional transducer pairs 206 without departing from the scope hereof. Each transducer pair 206 includes an inverted ultrasound transducer 208 and a non-inverted ultrasound transducer 210 joined to a radiating element 212, which is symbolically depicted by a dashed line in FIG. 2. Radiating element 212 is formed, for example, of at least one of one of quartz, sapphire, stainless steel, titanium, tantalum, boron nitride, silicon carbide, silicon nitride, aluminum and a ceramic material. In some embodiments, radiating element 212 is part, e.g., a wall or plate, of a tank for containing a liquid. In yet some other embodiments, radiating element 212 is omitted, such as in applications where ultrasound transducers 208 and non-inverted ultrasound transducers 210 are immersed in a liquid.

Each non-inverted ultrasound transducer 210 includes N piezoelectric elements (not shown), and each inverted ultrasound transducer 208 includes N corresponding piezoelectric elements (not shown), where N is an integer greater than or equal to one. In each transducer pair 206, the one or more piezoelectric elements of inverted ultrasound transducer 208 are flipped relative to the orientation of each corresponding piezoelectric element of non-inverted ultrasound transducer 210, with respect to radiating element 212. For example, in one embodiment, each inverted ultrasound transducer 208 includes a piezoelectric element having a positive pole facing in a direction 220 away from radiating element 212, and each non-inverted ultrasound transducer 210 includes a piezoelectric element having a positive pole facing in an opposite direction 222 toward radiating element 212. As another example, in another embodiment, each inverted ultrasound transducer 208 includes a piezoelectric element having a positive pole facing in direction 222 toward radiating element 212, and each non-inverted ultrasound transducer 210 includes a piezoelectric element having a positive pole facing in direction 220 away from radiating element 212. As yet another example, in FIG. 18 (discussed below), piezoelectric element 1530 is flipped relative to the orientation of corresponding piezoelectric element 1540, and piezoelectric element 1832 is flipped relative to the orientation of corresponding piezoelectric element 1842.

In each transducer pair 206, inverted ultrasound transducer 208 is electrically coupled in series with non-inverted ultrasound transducer 210. For example, in the depicted embodiment, the positive pole of each non-inverted ultrasound transducer 210 is electrically coupled to the negative pole of each inverted ultrasound transducer 208, and in an alternate embodiment, the negative pole of each non-inverted ultrasound transducer 210 is electrically coupled to the positive pole of each inverted ultrasound transducer 208.

Signal generator 204 includes an AC electrical power source 214 electrically coupled in series with a resonant inductor 216. Wiring 218 electrically couples each transducer pair 206 to signal generator 204. The configuration of signal generator 204 can vary without departing from the scope hereof. For example, in one alternate embodiment, resonant inductor 216 is electrically coupled in parallel with AC electrical power source 214, instead of in series with AC electrical power source 214. As another example, in another alternate embodiment, resonant inductor 216 is omitted, and ultrasound system 200 relies on parasitic inductance of an electrical circuit including ultrasound transducer array 202, signal generator 204, and wiring 218, for resonant inductance.

Signal generator 204 drives each transducer pair 206 with an electrical signal. The fact that each transducer pair 206 includes an inverted ultrasound transducer 208 and a non-inverted ultrasound transducer 210 electrically coupled in series causes the one or more piezoelectric elements of inverted ultrasound transducers 208 and the one or more piezoelectric elements of non-inverted ultrasound transducers 210 to expand and contract together when driven by the electrical signal. For example, in one embodiment, the one or more piezoelectric elements of each of inverted ultrasound transducers 208 and non-inverted ultrasound transducers 210 contract together during a positive portion of the electrical signal from signal generator 204, and the one or more piezoelectric elements of each of inverted ultrasound transducers 208 and non-inverted ultrasound transducers 210 expand together during a negative portion of the electrical signal from signal generator 204. As another example, in another embodiment, the one or more piezoelectric elements of each of inverted ultrasound transducers 208 and non-inverted ultrasound transducers 210 expand together during a positive portion of the electrical signal from signal generator 204, and the one or more piezoelectric elements of each of inverted ultrasound transducers 208 and non-inverted ultrasound transducers 210 contract together during a negative portion of the electrical signal from signal generator 204.

Simultaneous expansion or contraction of all piezoelectric elements of ultrasound transducer array 202, which is achieved by the configuration of transducer pairs 206, results in sound generation. If transducer pairs 206 were modified to include two ultrasound transducers of the same type e.g., two non-inverted ultrasound transducers or two inverted ultrasound transducers, the two ultrasound transducers in each transducer pair 206 would operate in opposing manners.

In some embodiments, signal generator 204 drives transducer pairs 206 with an electrical signal at a single frequency, while in some other embodiments, signal generator 204 drives transducer pairs 206 with an electrical signal at two or more frequencies. For example, in some embodiments, signal generator 204 sweeps the frequency of the electrical signal with respect to a base frequency. In certain embodiments, the base frequency is a center frequency of a sweep frequency range, and signal generator 204 sweeps the frequency of the electrical signal within a predetermined percentage of the base frequency, e.g., within two percent, ten percent, or twenty percent, of the base frequency. In some other embodiments, signal generator 204 sweeps the frequency of the electrical signal in an asymmetric manner with respect to the base frequency, such that the base frequency is offset from the center frequency of the sweep frequency range. In particular embodiments, signal generator 204 sweeps the frequency of the electrical signal with respect to a base frequency according to a triangle function, a saw tooth function, a stair-step function, a dual-sweep function, or a random function. Applicant has found that sweeping the frequency of the electrical signal generated by signal generator 204 can achieve significant advantages in some applications.

The series electrical connection of inverted ultrasound transducer 208 and non-inverted ultrasound transducer 210 in each transducer pair 206 promotes low capacitance of ultrasound transducer array 202. For example, consider an embodiment where each inverted ultrasound transducer 208 and each non-inverted ultrasound transducer 210 has a respective capacitance value $C_1$. Ultrasound transducer array 202 will have a net capacitance $C_{net\_202}$ according to EQN. 2 below, in this embodiment.

$$C_{net\_202} = \frac{C_1}{2} + \frac{C_1}{2} = C_1 \qquad \text{(EQN. 2)}$$

Thus, net capacitance $C_{net\_202}$ of this embodiment of ultrasound transducer array 202 is equal to the capacitance value of one ultrasound transducer instance. Now consider conventional ultrasound transducer array 102 of FIG. 1, assuming that each ultrasound transducer 108 also has a respective capacitance value $C_1$. Ultrasound transducer array 102 will have a net capacitance $C_{net\_102}$ according to EQN. 3 below.

$$C_{net\_102} = C_1 + C_1 + C_1 + C_1 = 4C_1 \qquad \text{(EQN. 3)}$$

As evident when comparing EQNS. 2 and 3, the above-discussed embodiment of the new ultrasound transducer array 202 has one quarter of the capacitance of conventional ultrasound transducer array 102, even though both transducer arrays have the same number of ultrasound transducers. Accordingly, ultrasound transducer array 202 achieves much lower capacitance values than conventional ultrasound transducer arrays having like numbers of ultrasound transducers of similar respective capacitance values.

Figure 3:
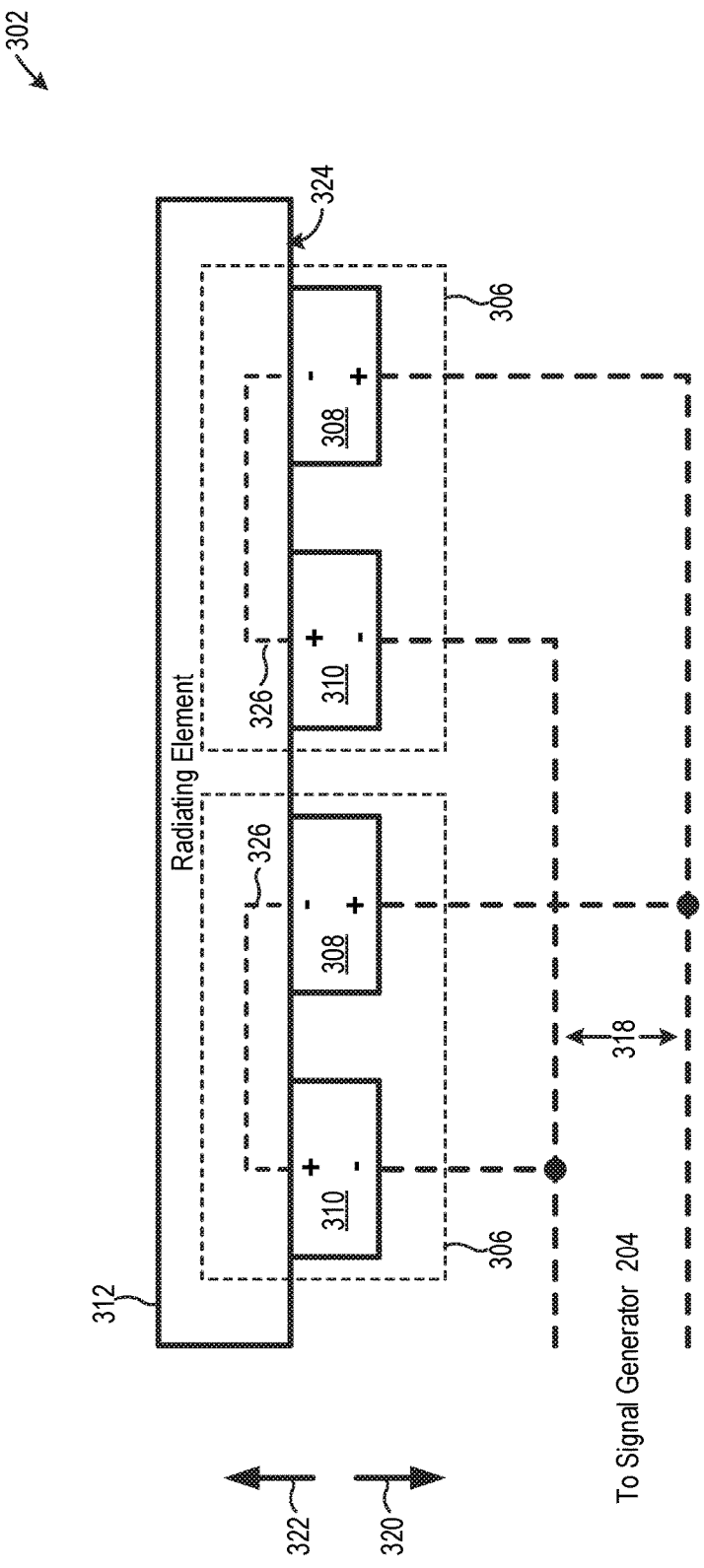
FIG. 3 is a side elevation view illustrating an example embodiment of an ultrasound transducer array of the FIG. 2 ultrasound system.
Figure 4:
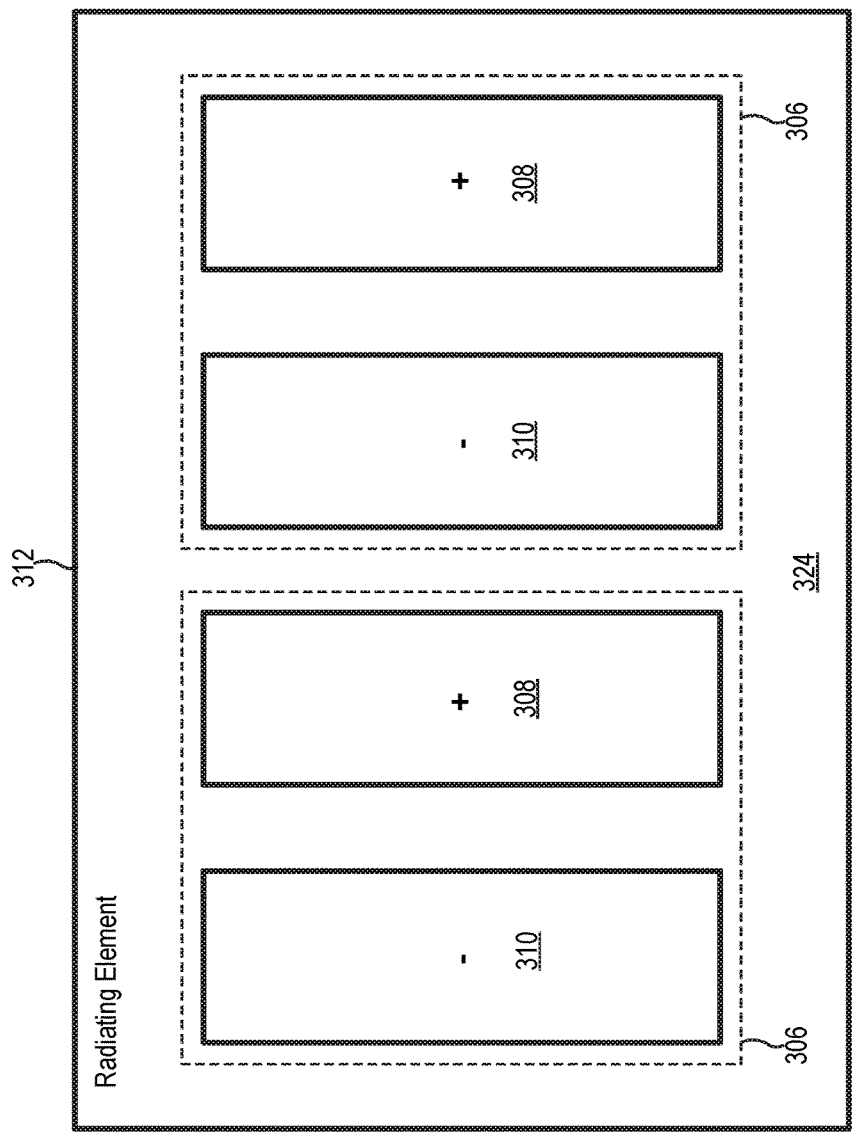
FIG. 4 is a bottom plan view of the FIG. 3 ultrasound transducer array.

FIG. 3 is a side elevation view of one embodiment of ultrasound transducer array 302, and FIG. 4 is a bottom plan view of ultrasound transducer array 302. Ultrasound transducer array 302 is an example embodiment of ultrasound transducer array 202 (FIG. 2), where ultrasound transducers are implemented by piezoelectric elements. Certain embodiments of ultrasound transducer array 302 are capable of operating at megasonic frequencies. Ultrasound transducer array 302 includes a plurality of transducer pairs 306, a radiating element 312, and wiring 318, which are analogous to transducer pairs 206, radiating element 212, and wiring 218 of FIG. 2. The number of transducer pairs 306 could be increased without departing from the scope hereof. Wiring 318 electrically couples transducer pairs 306 in parallel, such that like polarities of piezoelectric elements are connected together. Wiring 318 is symbolically shown by dashed lines in FIG. 3, and the physical configuration of wiring 318 could accordingly vary from the physical configuration depicted in FIG. 3 without departing from the scope hereof. Wiring 318 is not shown in the FIG. 4 bottom plan view to promote illustrative clarity.

Each transducer pair 306 includes an inverted piezoelectric element 308 and a non-inverted piezoelectric element 310, which are embodiments of inverted ultrasound transducer 208 and non-inverted ultrasound transducer 210, respectively. Each inverted piezoelectric element 308 and each non-inverted piezoelectric element 310 is formed, for example, of a piezoelectric ceramic material. Inverted piezoelectric elements 308 are joined to an outer surface 324 of radiating element 312 such that their positive poles face a first direction, and non-inverted piezoelectric elements 310 are joined to outer surface 324 such that their positive poles face a second direction that is opposite of the first direction. For example, in the illustrated embodiment, the positive pole of each inverted piezoelectric element 308 faces a direction 320 away from radiating element 312, and the positive pole of each non-inverted piezoelectric element 310 faces a direction 322 towards radiating element 312 (see FIG. 3). In an alternate embodiment, the positive pole of each inverted piezoelectric elements 308 faces direction 322, and the positive pole of each non-inverted piezoelectric elements 310 faces direction 320.

Within each transducer pair 306, inverted piezoelectric element 308 is electrically coupled to non-inverted piezoelectric element 310 in series by an electrical conductor 326. For example, within each transducer pair 306 of the depicted embodiment, the positive pole of non-inverted piezoelectric element 310 is electrically coupled to the negative pole of inverted piezoelectric element 308, and in an alternate embodiment, the negative pole of non-inverted piezoelectric element 310 is electrically coupled to the positive pole of inverted piezoelectric element 308. Electrical conductors 326 are symbolically shown by dashed lines in FIG. 3, and the physical configuration of electrical conductors 326 could accordingly vary from the physical configuration depicted in FIG. 3 without departing from the scope hereof. Electrical conductors 326 are not shown in the FIG. 4 bottom plan view to promote illustrative clarity.

In certain embodiments, radiating element 312 forms at least a part of electrical conductors 326. For example, in some embodiments, electrical conductors 326 are implemented by electrical conductors embedded in radiating element 312 or by electrical conductors disposed on outer surface 324 of radiating element 312. In some other embodiments, electrical conductors 326 are separate from radiating element 312. In yet other embodiments, radiating element 312 is electrically conductive and serves as electrical conductors 326.

Discussed below with respect to FIGS. 5-13 are several example embodiments of inverted piezoelectric element 308 and non-inverted piezoelectric element 310. It should be realized, however, that inverted piezoelectric element 308 and non-inverted piezoelectric element 310 are not limited to these particular embodiments.

Figures 5, 6:
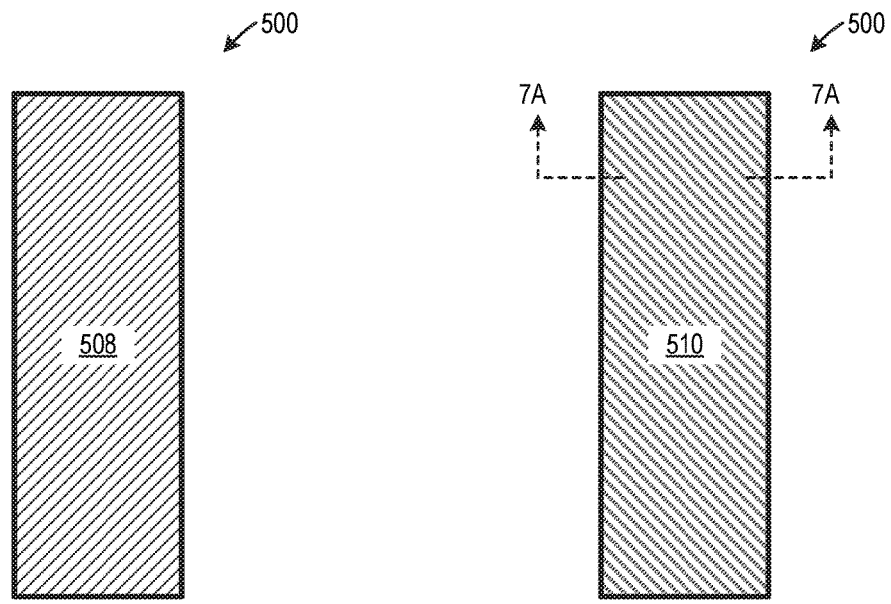
FIG. 5 is a top plan view of a piezoelectric element, according to an embodiment.
FIG. 6 is a bottom plan view of the FIG. 5 piezoelectric element.
Figure 7:
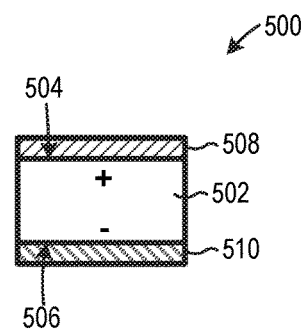
FIG. 7 is a cross-sectional view of the FIG. 5 piezoelectric element taken along line 7A-7A of FIG. 6.

FIG. 5 is a top plan view and FIG. 6 is a bottom plan view of a piezoelectric element 500. FIG. 7 is a cross-sectional view of piezoelectric element 500 taken along line 7A-7A of FIG. 6. Piezoelectric element 500 can serve as either inverted piezoelectric element 308 or non-inverted piezoelectric element 310, depending on how it is joined to radiating element 312, as discussed below. Piezoelectric element 500 includes a body 502 formed of a piezoelectric material, e.g., a ceramic piezoelectric material, having a first outer surface 504 and an opposing second outer surface 506. A first electrode 508 is disposed on first outer surface 504 adjacent to a positive pole of piezoelectric element 500, and a second electrode 510 is disposed on second outer surface 506 adjacent to a negative pole of piezoelectric element 500. First and second electrodes 508 and 510 provide electrical interface to the first and second poles, respectively.

Piezoelectric element 500 can serve as inverted piezoelectric element 308 when joined to radiating element 312 such that its negative pole faces radiating element 312. Additionally, piezoelectric element 500 can serve as non-inverted piezoelectric element 310 when affixed to radiating element 312 such that its positive pole faces radiating element 312. In an alternate embodiment, piezoelectric element 500 can serve as inverted piezoelectric element 308 when joined to radiating element 312 such that its positive pole faces radiating element 312. Additionally, piezoelectric element 500 can serve as non-inverted piezoelectric element 310 when affixed to radiating element 312 such that its negative pole faces radiating element 312.

FIG. 8 is a top plan view and FIG. 9 is a bottom plan view of a piezoelectric element 800. FIG. 10 is an elevation view of an end 811 of piezoelectric element 800. Piezoelectric element 800 can serve as non-inverted piezoelectric element 310. Piezoelectric element 800 includes a body 802 formed of a piezoelectric material, e.g., a ceramic piezoelectric material, having a first outer surface 804 and an opposing second outer surface 806 separated from each other in a thickness 808 direction. A first electrode 810 is disposed on first outer surface 804 adjacent to a positive pole of piezoelectric element 800, and first electrode 810 wraps around end 811 to second outer surface 806. A second electrode 812 is disposed on second outer surface 806 adjacent to a negative pole of piezoelectric element 800. First electrode 810 and second electrode 812 are separated from each other by an insulated region 814.

First and second electrodes 810 and 812 provide electrical interface to the positive and negative poles, respectively. The fact that first and second electrodes 810 and 812 are accessible from a common side of piezoelectric element 800 enables all external electrical connections, e.g., connections to wiring 318 and electrical conductors 326, to be on the common side of piezoelectric element 800. The shape and location of first and second electrodes 810 and 812 could vary without departing from the scope hereof.

FIG. 11 is a top plan view and FIG. 12 is a bottom plan view of a piezoelectric element 1100. FIG. 13 is an elevation view of an end 1111 of piezoelectric element 1100. Piezoelectric element 1100 can serve as inverted piezoelectric element 308. Piezoelectric element 1100 includes a body 1102 formed of a piezoelectric material, e.g., a ceramic piezoelectric material, having a first outer surface 1104 and an opposing second outer surface 1106 separated from each other in a thickness 1108 direction. A first electrode 1110 is disposed on first outer surface 1104 adjacent to a negative pole of piezoelectric element 1100, and first electrode 1110 wraps around end 1111 to second outer surface 1106. A second electrode 1112 is disposed on second outer surface 1106 adjacent to a positive pole of piezoelectric element 1100. First electrode 1110 and second electrode 1112 are separated from each other by an insulated region 1114.

First and second electrodes 1110 and 1112 provide electrical interface to the negative and positive poles, respectively. The fact that first and second electrodes 1110 and 1112 are accessible from a common side of piezoelectric element 1100 enables all external electrical connections, e.g., connections to wiring 318 and electrical conductors 326, to be on the common side of piezoelectric element 1100. The shape and location of first and second electrodes 1110 and 1112 could vary without departing from the scope hereof.

Figure 14:
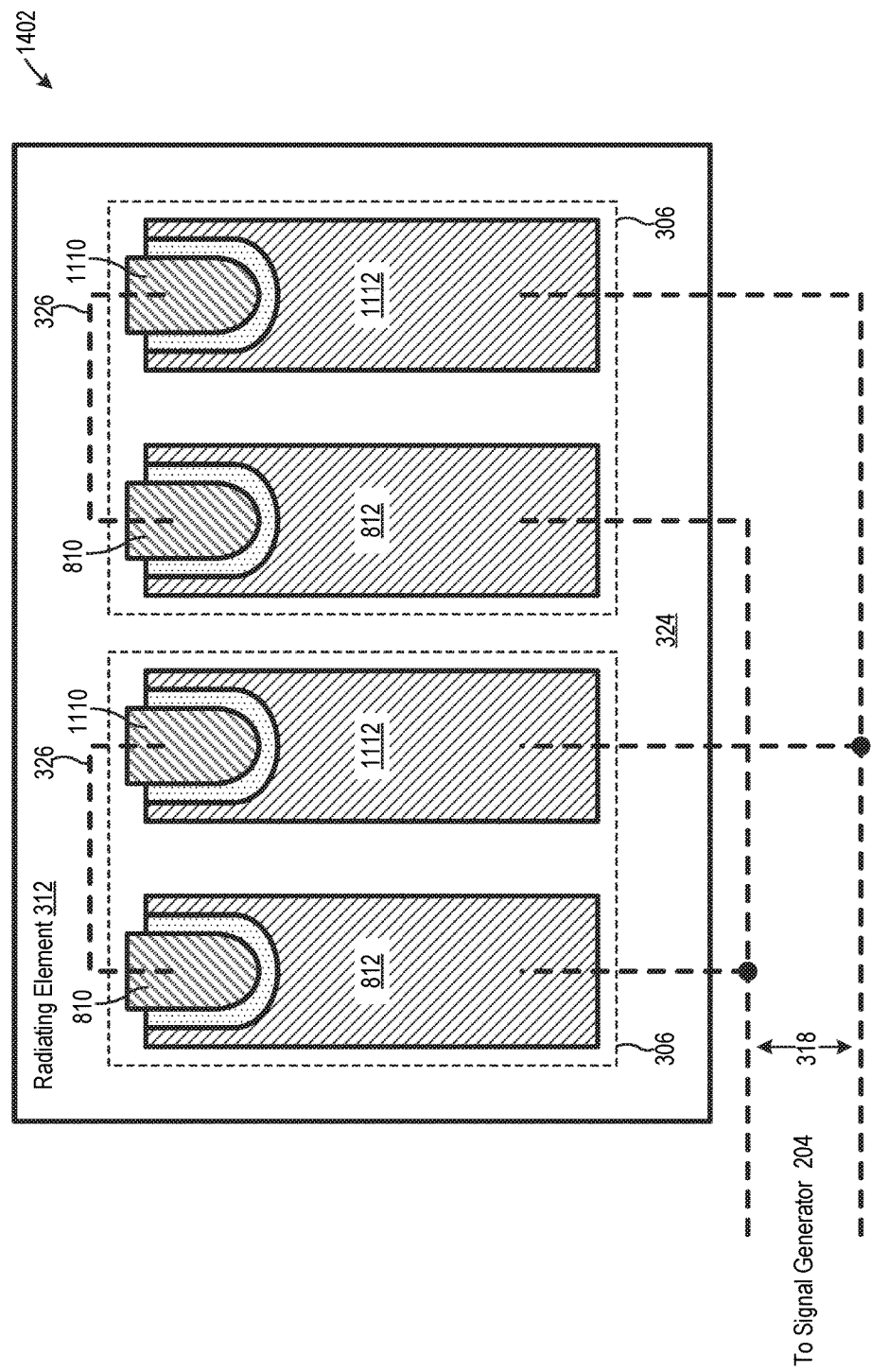
FIG. 14 is a bottom plan view of an embodiment of the FIG. 3 ultrasound transducer array including the piezoelectric elements of FIGS. 8-13.

FIG. 14 is a bottom plan view of an ultrasound transducer array 1402, which is an embodiment of ultrasound transducer array 302 where inverted and non-inverted piezoelectric elements 308 and 310 are embodied by piezoelectric elements 1100 and 800, respectively. In certain embodiments of ultrasound transducer array 1402, radiating element 312 is formed of quartz or another non-conductive material.

Figure 15:
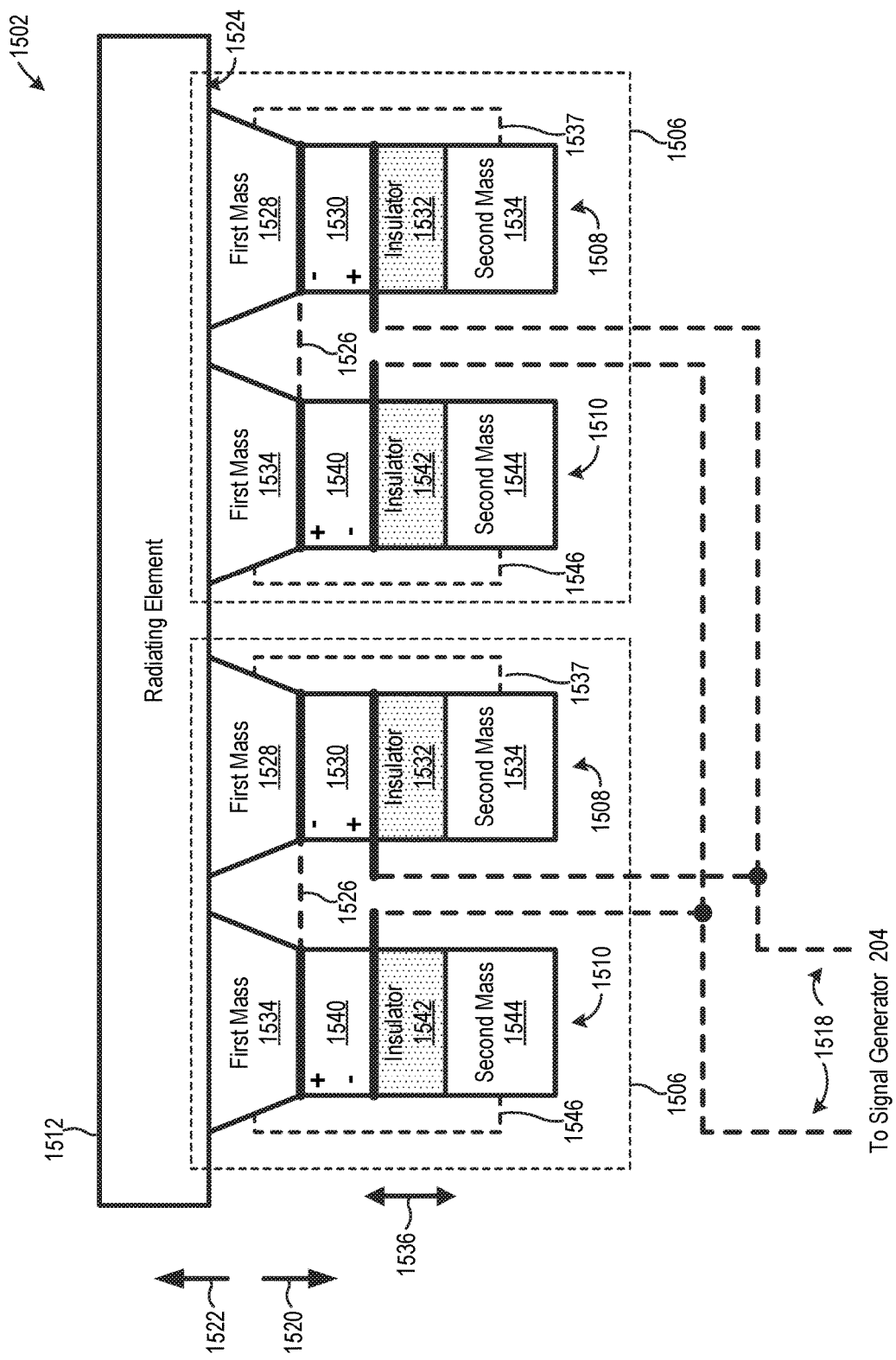
FIG. 15 is a side elevation view illustrating another example embodiment of an ultrasound transducer array of the FIG. 2 ultrasound system.
Figure 16:
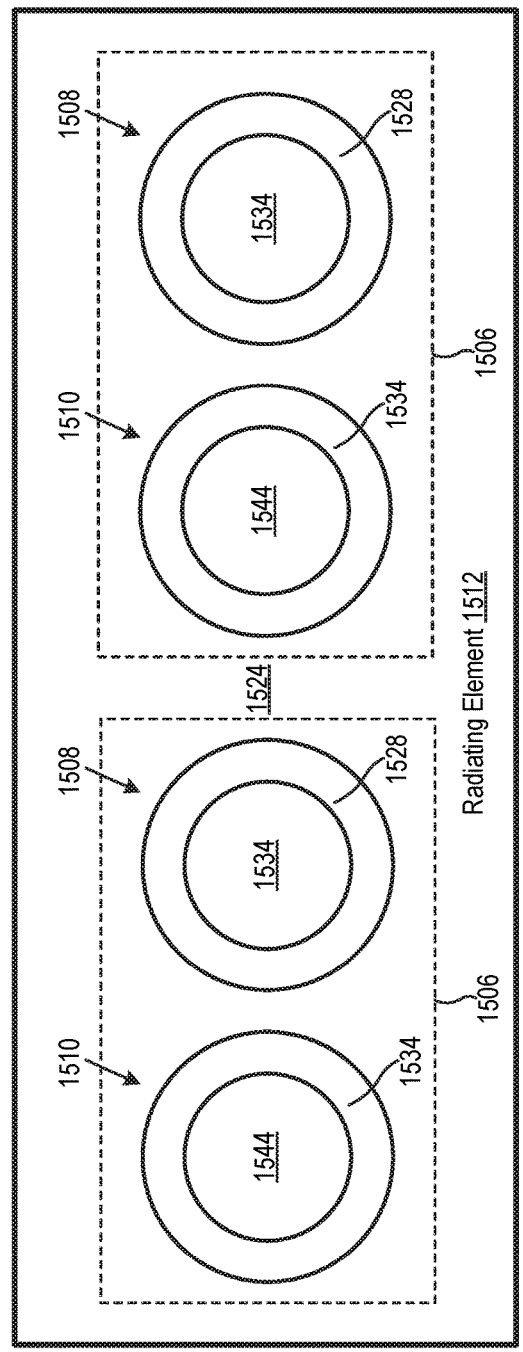
FIG. 16 is a bottom plan view of the FIG. 15 ultrasound transducer array.

FIG. 15 is a side elevation view of an ultrasound transducer array 1502, and FIG. 16 is a bottom plan view of ultrasound transducer array 1502. Ultrasound transducer array 1502 is an example embodiment of ultrasound transducer array 202 (FIG. 2), where ultrasound transducers are implemented by Langevin assemblies. Ultrasound transducer array 1502 includes a plurality of transducer pairs 1506, a radiating element 1512, and wiring 1518, which are analogous to transducer pairs 206, radiating element 212, and wiring 218 of FIG. 2. The number of transducer pairs 1506 could be increased without departing from the scope hereof. Wiring 1518 electrically couples transducer pairs 1506 in parallel, such that like polarities of piezoelectric elements are connected together. Wiring 1518 is symbolically shown by dashed lines in FIG. 15, and the physical configuration of wiring 1518 could accordingly differ from the physical configuration depicted in FIG. 15 without departing from the scope hereof. Wiring 1518 is not shown in the FIG. 16 bottom plan view to promote illustrative clarity.

Each transducer pair 1506 includes an inverted Langevin assembly 1508 and a non-inverted Langevin assembly 1510, which are embodiments of inverted ultrasound transducer 208 and non-inverted ultrasound transducer 210, respectively. Each inverted Langevin assembly 1508 and each non-inverted Langevin assembly 1510 is affixed to an outer surface 1524 of radiating member 1512. Each inverted Langevin assembly 1508 includes a first mass 1528, a piezoelectric element 1530, an insulator 1532, and a second mass 1534, stacked in a thickness direction 1536. Piezoelectric element 1530 is formed, for example, of a piezoelectric ceramic material, and piezoelectric element 1530 includes a positive pole and a negative pole. Piezoelectric element 1530 is disposed in inverted Langevin assembly 1508 such that its positive pole faces away from radiating element 1512 in a direction 1520 which is parallel to thickness direction 1536. Piezoelectric element 1530 is disposed between first mass 1528 and insulator 1532 in thickness direction 1536, and insulator 1532 is disposed between piezoelectric element 1530 and second mass 1534 in thickness direction 1536. First mass 1528 is electrically coupled to second mass 1534, e.g., by a bolt mechanically connecting first mass 1528 to second mass 1534, as symbolically shown by a dashed line 1537 in FIG. 15.

Each non-inverted Langevin assembly 1510 includes a first mass 1534, a piezoelectric element 1540, an insulator 1542, and a second mass 1544 stacked in thickness direction 1536. Piezoelectric element 1540 is formed, for example, of a piezoelectric ceramic material, and piezoelectric element 1540 includes a positive pole and a negative pole. Piezoelectric element 1540 is disposed in non-inverted Langevin assembly 1510 such that its positive pole faces toward radiating element 1512 in a direction 1522 which is parallel to thickness direction 1536. Piezoelectric element 1540 is disposed between first mass 1534 and insulator 1542 in thickness direction 1536, and insulator 1542 is disposed between piezoelectric element 1540 and second mass 1544 in thickness direction 1536. First mass 1534 is electrically coupled to second mass 1544, e.g., by a bolt mechanically connecting first mass 1534 to second mass 1544, as symbolically shown by a dashed line 1546 in FIG. 15.

Within each transducer pair 1506, inverted Langevin assembly 1508 is electrically coupled to non-inverted inverted Langevin assembly 1510 in series by an electrical conductor 1526, such that a positive pole of non-inverted Langevin assembly 1510 is electrically coupled to a negative pole of inverted Langevin assembly 1508. In an alternate embodiment, the negative pole of non-inverted Langevin assembly 1510 is electrically coupled to the positive pole of inverted Langevin assembly 1508. Electrical conductors 1526 are symbolically shown by dashed lines in FIG. 15, and the physical configuration of electrical conductors 1526 could accordingly vary from the physical configuration depicted in FIG. 15 without departing from the scope hereof.

For example, the radiating element 1512 can be used as the electrical conductors 1526. Electrical conductors 1526 are not shown in the FIG. 16 bottom plan view to promote illustrative clarity.

In an alternate embodiment, the positive pole of piezoelectric element 1530 in each inverted Langevin assembly 1508 faces direction 1522, and the positive pole of piezoelectric element 1540 of each non-inverted Langevin assembly 1510 faces direction 1520. Thus, the polarity of Langevin assemblies in ultrasonic transducer array 1502 can be generally described as follows: (a) the positive pole of piezoelectric element 1530 in each inverted Langevin assembly 1508 faces a first direction, and (b) the positive pole of piezoelectric element 1540 of each non-inverted Langevin assembly 1510 faces a second direction that is opposite of the first direction.

Figure 17:
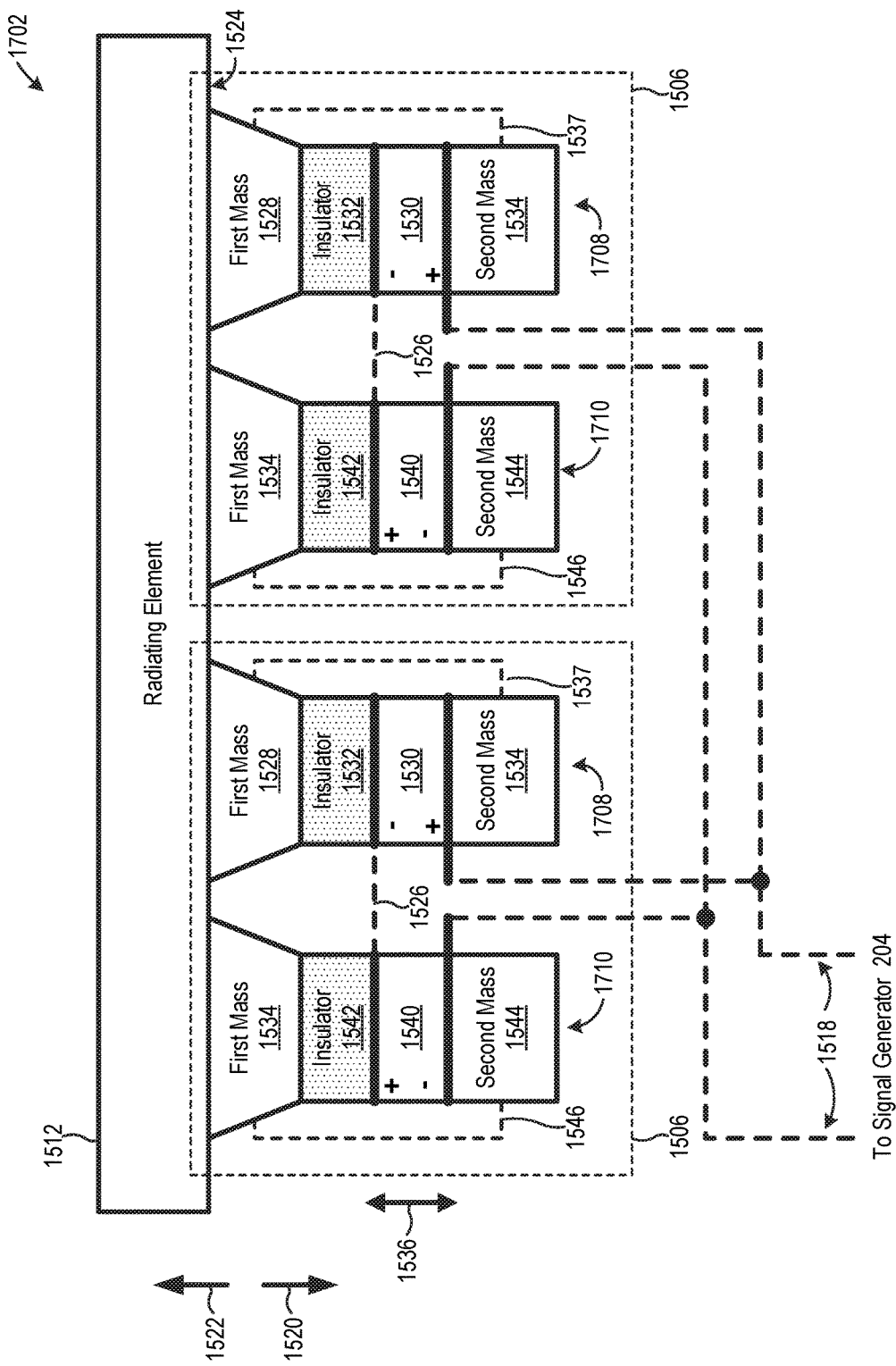
FIG. 17 is a side elevation view illustrating yet another example embodiment of an ultrasound transducer array of the FIG. 2 ultrasound system.

FIG. 17 is a side elevation view of an ultrasonic transducer array 1702, which is like ultrasound transducer array 1500 of FIGS. 15 and 16, but with inverted Langevin assemblies 1508 and non-inverted Langevin assemblies 1510 replaced by inverted Langevin assemblies 1708 and non-inverted Langevin assemblies 1710, respectively. Inverted Langevin assembly 1708 is like inverted Langevin assembly 1508 but with the positions of insulator 1532 and piezoelectric element 1530 swapped. Consequently, insulator 1532 is disposed between first mass 1528 and piezoelectric element 1530, and piezoelectric element 1530 is disposed between insulator 1532 and second mass 1534, in inverted Langevin assembly 1708. Similarly, non-inverted Langevin assembly 1710 is like non-inverted Langevin assembly 1510 but with the positions of insulator 1542 and piezoelectric element 1540 swapped. Consequently, insulator 1542 is disposed between first mass 1534 and piezoelectric element 1540, and piezoelectric element 1540 is disposed between insulator 1542 and second mass 1544, in non-inverted Langevin assembly 1710.

Figure 18:
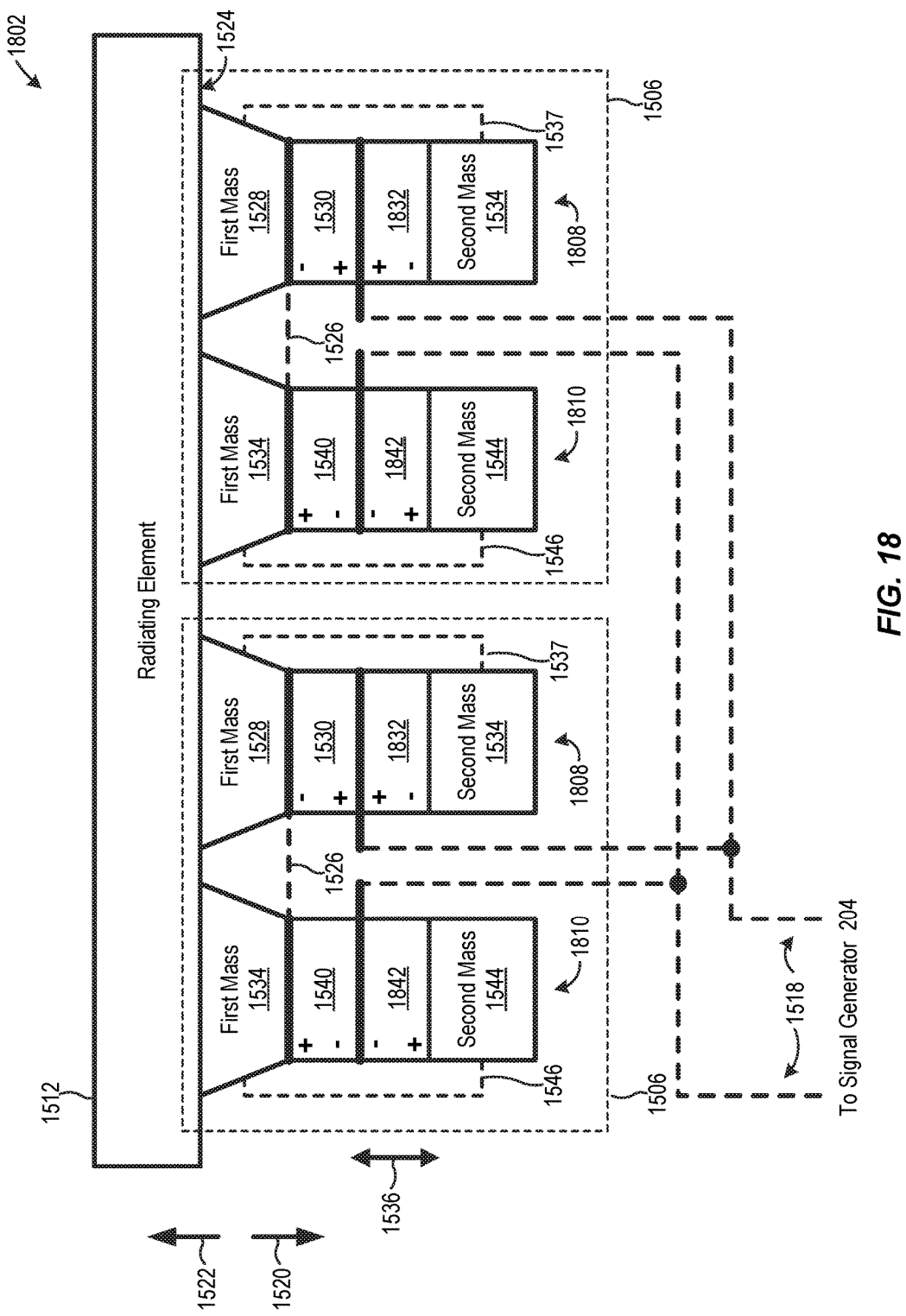
FIG. 18 is a side elevation view illustrating another example embodiment of an ultrasound transducer array of the FIG. 2 ultrasound system.

FIG. 18 is a side elevation view of an ultrasonic transducer array 1802, which is like ultrasound transducer array 1500 of FIGS. 15 and 16, but with inverted Langevin assemblies 1508 and non-inverted Langevin assemblies 1510 replaced by inverted Langevin assemblies 1808 and non-inverted Langevin assemblies 1810, respectively. Inverted Langevin assembly 1808 is like inverted Langevin assembly 1508 but with insulator 1532 replaced with a piezoelectric element 1832. Consequently, piezoelectric element 1530 is disposed between first mass 1528 and piezoelectric element 1832, and piezoelectric element 1832 is disposed between piezoelectric element 1530 and second mass 1534, in inverted Langevin assembly 1808. Piezoelectric element 1530 and piezoelectric element 1832 are electrically coupled in parallel with each other within inverted Langevin assembly 1808. In inverted Langevin assembly 1808, piezoelectric element 1530 and piezoelectric element 1832 have respective positive poles facing towards each other. Piezoelectric elements 1530 and 1832 expand and contract together when driven by an electrical signal, e.g., an electrical signal from signal generator 204.

Similarly, non-inverted Langevin assembly 1810 is like non-inverted Langevin assembly 1510 but with insulator 1542 replaced with a piezoelectric element 1842. Consequently, piezoelectric element 1540 is disposed between first mass 1534 and piezoelectric element 1842, and piezoelectric element 1842 is disposed between piezoelectric element 1540 and second mass 1544, in non-inverted Langevin assembly 1810. Piezoelectric element 1540 and piezoelectric element 1842 are electrically coupled in parallel with each other within non-inverted Langevin assembly 1810. In non-inverted Langevin assembly 1810, piezoelectric element 1540 and piezoelectric element 1842 have respective positive poles facing away from each other. Piezoelectric elements 1540 and 1842 expand and contract together when driven by an electrical signal, e.g., an electrical signal from signal generator 204.

Figure 19:
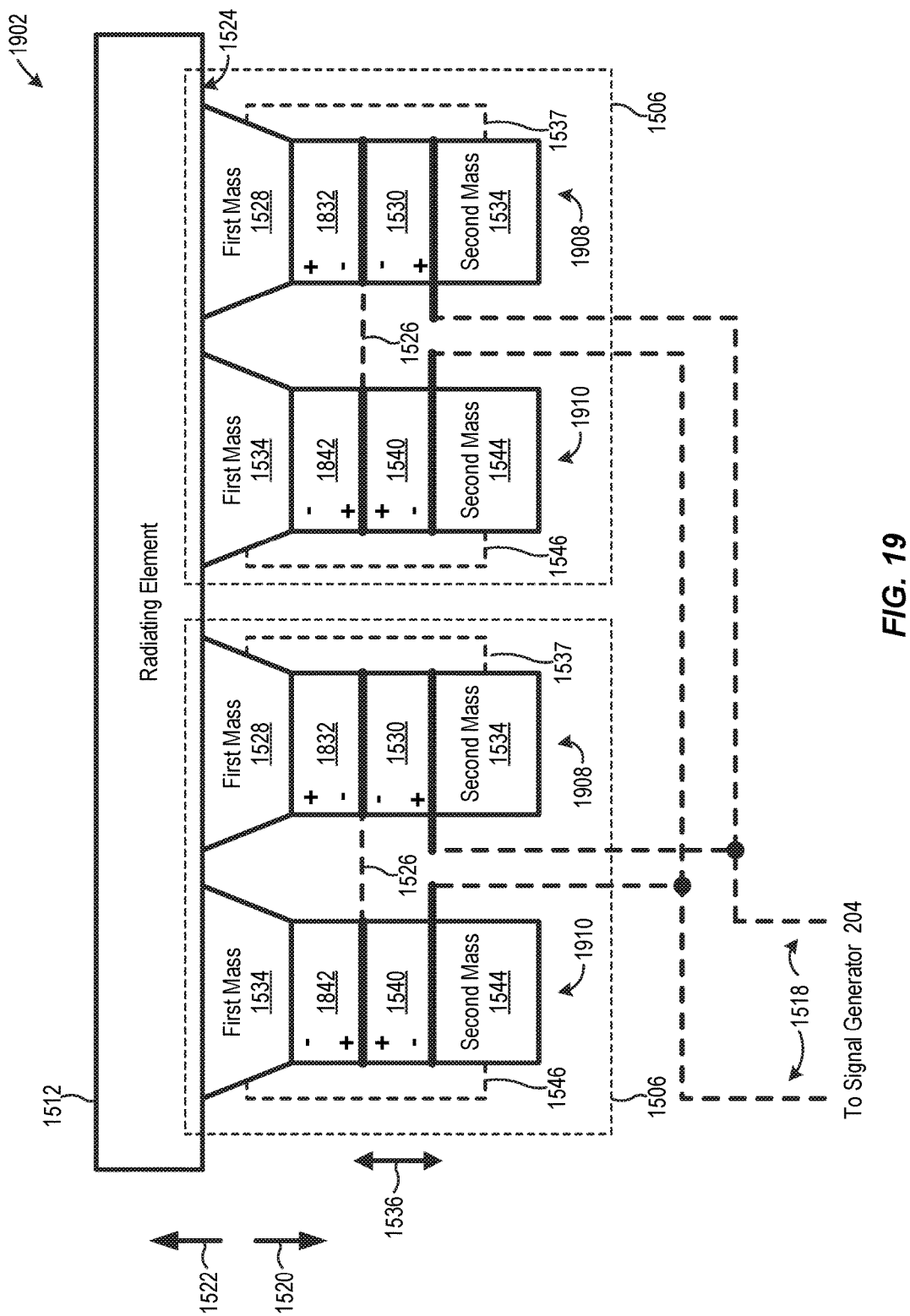
FIG. 19 is a side elevation view illustrating another example embodiment of an ultrasound transducer array of the FIG. 2 ultrasound system.

FIG. 19 is a side elevation view of an ultrasonic transducer array 1902, which is like ultrasound transducer array 1802 of FIG. 18, but with inverted Langevin assemblies 1808 and non-inverted Langevin assemblies 1810 replaced by inverted Langevin assemblies 1908 and non-inverted Langevin assemblies 1910, respectively. Inverted Langevin assembly 1908 is like inverted Langevin assembly 1808 but with the positions of piezoelectric elements 1530 and 1832 swapped. Consequently, piezoelectric element 1832 is disposed between first mass 1528 and piezoelectric element 1530, and piezoelectric element 1530 is disposed between piezoelectric element 1832 and second mass 1534, in inverted Langevin assembly 1908. Piezoelectric element 1530 and piezoelectric element 1832 are electrically coupled in parallel with each other within inverted Langevin assembly 1908. In inverted Langevin assembly 1908, piezoelectric element 1530 and piezoelectric element 1832 have respective positive poles facing away from each other.

Similarly, non-inverted Langevin assembly 1910 is like non-inverted Langevin assembly 1810 but with the positions of piezoelectric element 1842 and piezoelectric element 1540 swapped. Consequently, piezoelectric element 1842 is disposed between first mass 1534 and piezoelectric element 1540, and piezoelectric element 1540 is disposed between piezoelectric element 1842 and second mass 1544, in non-inverted Langevin assembly 1910. Piezoelectric element 1540 and piezoelectric element 1842 are electrically coupled in parallel with each other within non-inverted Langevin assembly 1910. In non-inverted Langevin assembly 1910, piezoelectric element 1540 and piezoelectric element 1842 have respective positive poles facing towards each other. In this embodiment, first mass 1534 is insulated from first mass 1528.

Figure 20:
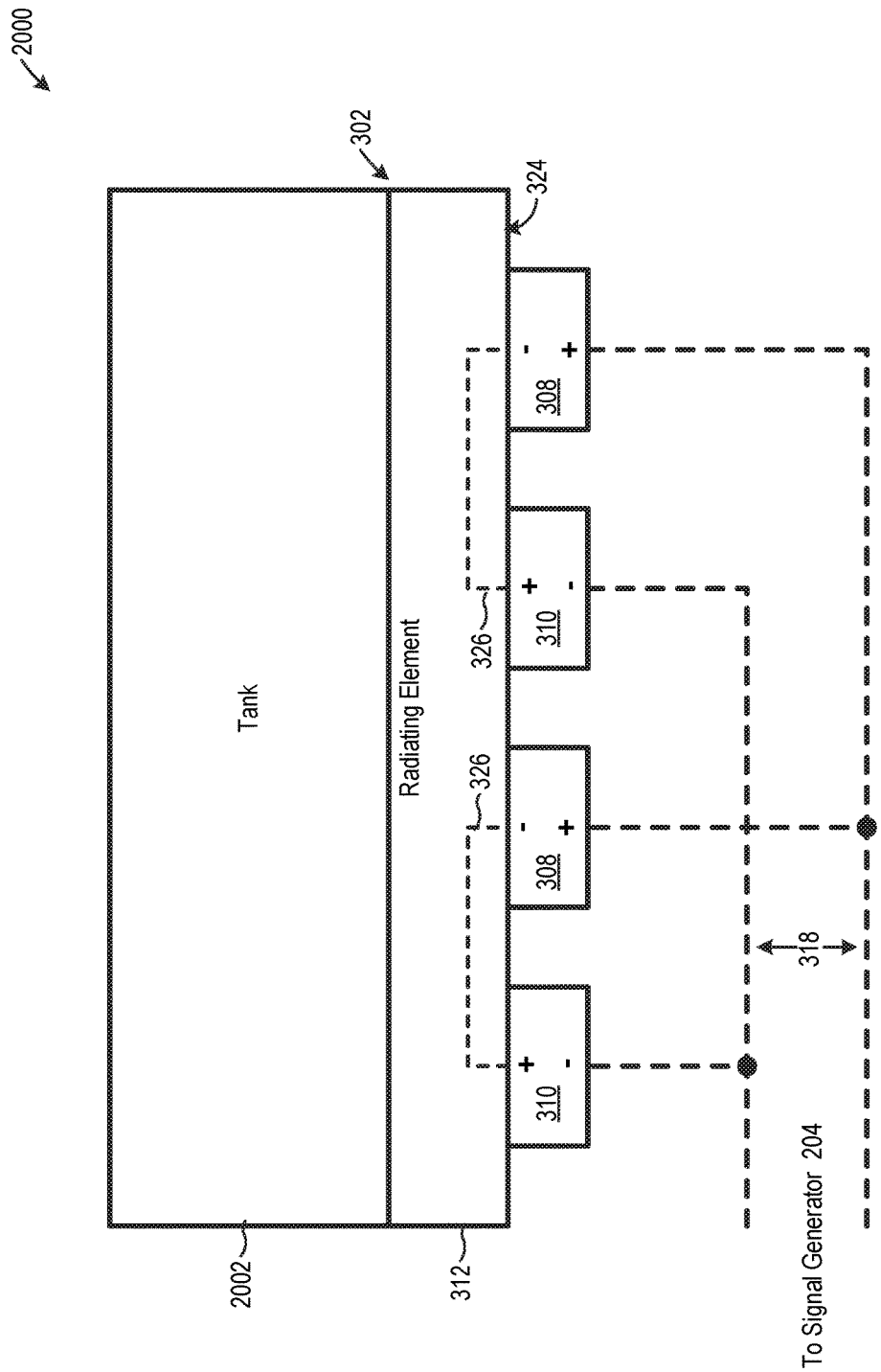
FIG. 20 is a side plan view of an ultrasound assembly including an instance of the FIG. 3 ultrasound transducer array affixed to a tank for containing a liquid, according to an embodiment.

In any of the new ultrasound transducer arrays disclosed herein, the radiating element is optionally affixed to a tank for containing a liquid, for coupling sonic energy from the ultrasound transducer array into the liquid. For example, FIG. 20 is a side plan view of an ultrasound assembly 2000 including an instance of ultrasound transducer array 302 affixed to a tank 2002 for containing a liquid. Ultrasound assembly 2000 is configured, for example, for cleaning an object in the liquid, processing the liquid, or inactivating organisms in the liquid. The other new ultrasound transducer arrays disclosed herein could be affixed to a tank in a similar manner.

Figure 21:
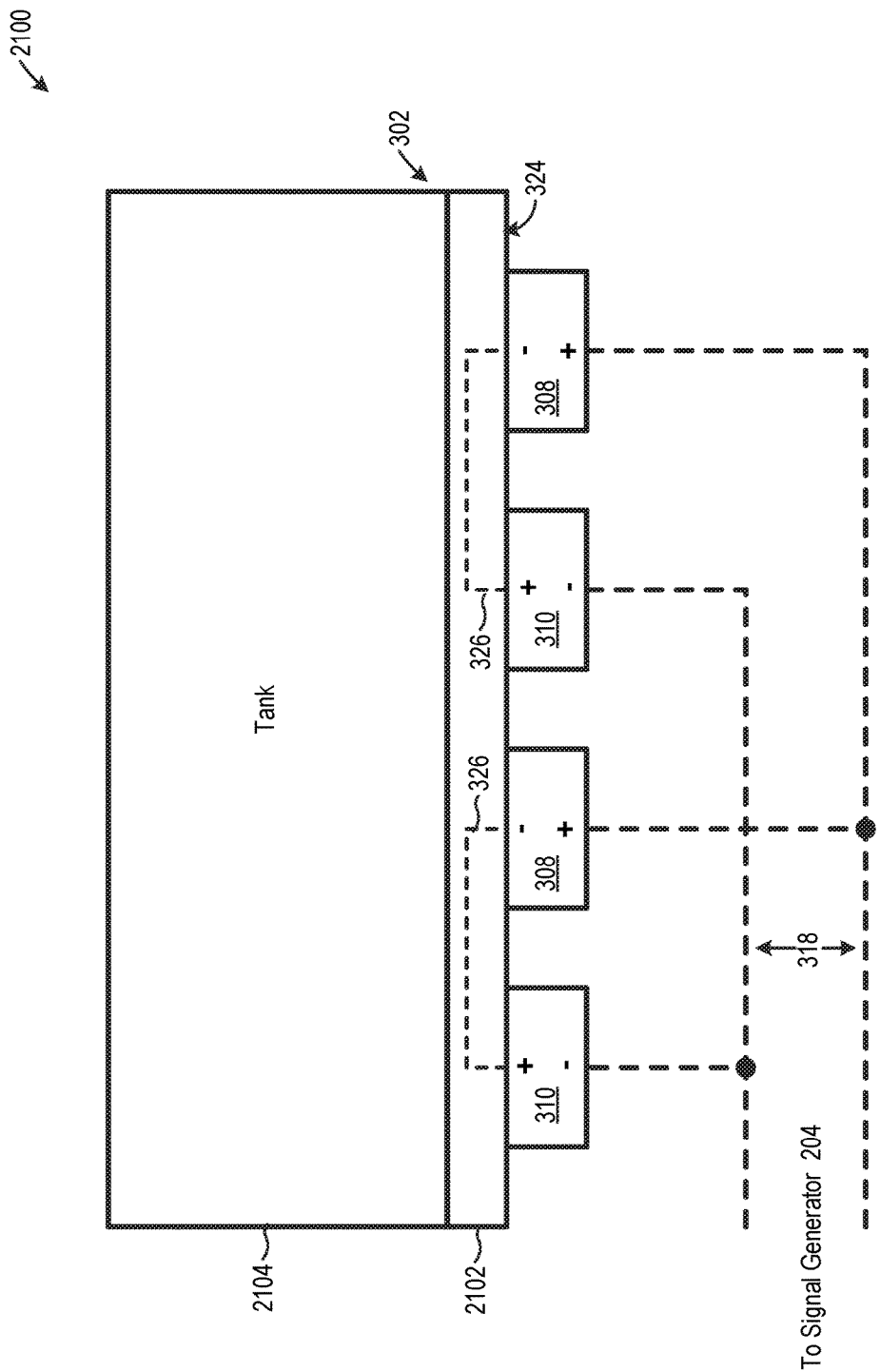
FIG. 21 is a side plan elevation of an ultrasound assembly including an instance of the FIG. 3 ultrasound transducer array where a radiating element of the ultrasound transducer array is implemented by a bottom plate of a tank, according to an embodiment.

Furthermore, in any of the new ultrasound transducer arrays disclosed herein, the radiating element is optionally a portion of a tank for containing a liquid, for coupling sonic energy from the ultrasound transducer array into the liquid. For example, FIG. 21 is a side elevation view of an ultrasound assembly 2100 including an instance of ultrasound transducer array 302 where radiating element 312 is implemented by a bottom plate 2102 of a tank 2104 for containing a liquid. Ultrasound assembly 2100 is configured, for example, for cleaning an object in the liquid, processing the liquid, or inactivating organisms in the liquid. The other new ultrasound transducer arrays disclosed herein could be configured in a similar manner.

Figure 22:
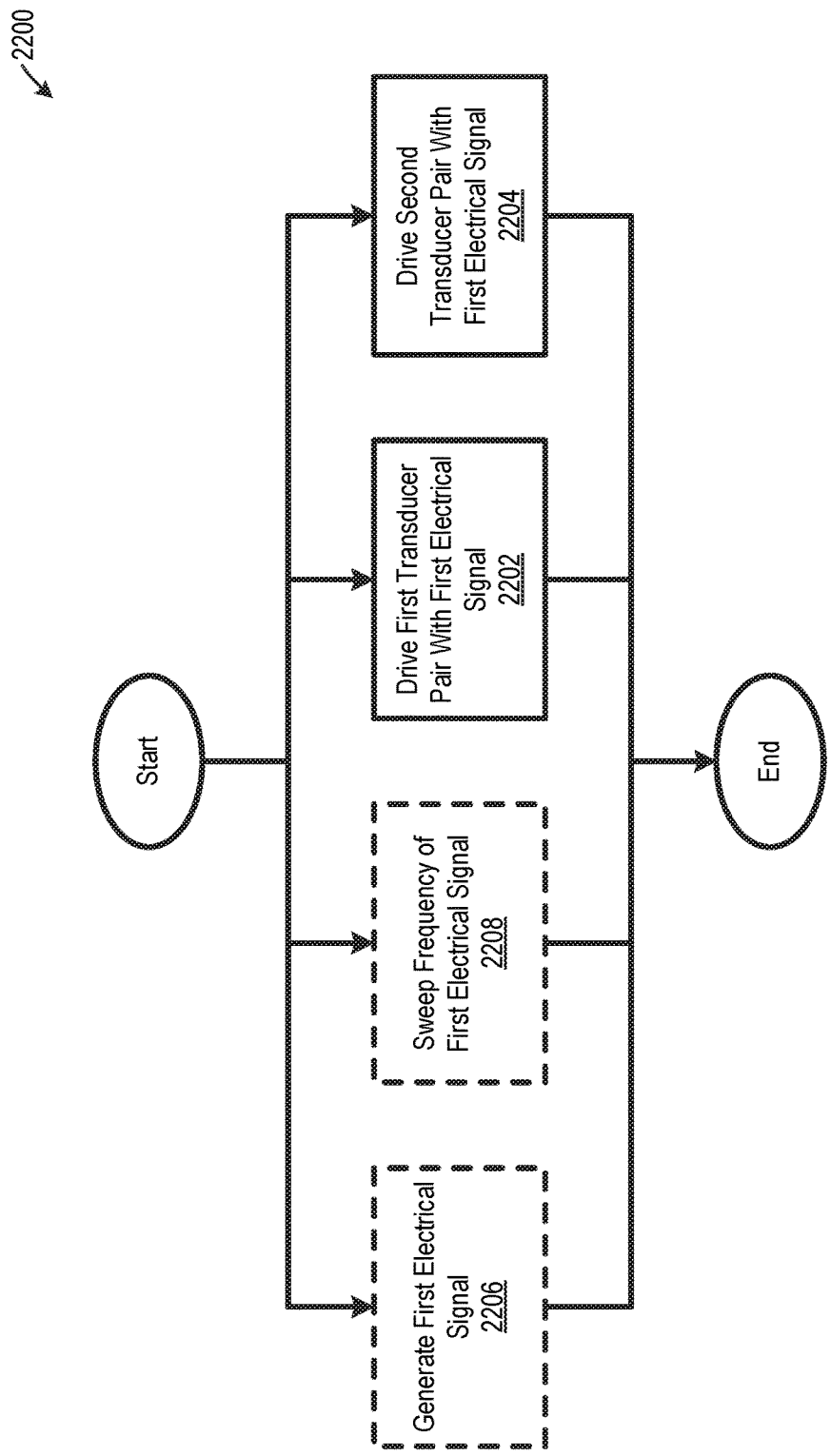
FIG. 22 is a flow chart illustrating a method for coupling sonic energy into a liquid, according to an embodiment.

FIG. 22 is a flow chart illustrating a method 2200 for coupling sonic energy into a liquid. Method 2200 includes steps 2202 and 2204 which are executed in parallel. In step 2202, a first transducer pair is driven with a first electrical signal, where the first transducer pair includes a first inverted ultrasound transducer and a first non-inverted ultrasound transducer electrically coupled in series. In one example of step 2202, the left transducer pair 206 illustrated in FIG. 2 is driven with an electrical signal from signal generator 204. In step 2204, a second transducer pair is driven with the first electrical signal, where the second transducer pair is electrically coupled in parallel with the first transducer pair, and where the second transducer pair includes a second inverted ultrasound transducer and a second non-inverted ultrasound transducer electrically coupled in series. In one example of step 2204, the right transducer pair 206 illustrated in FIG. 2 is driven with the electrical signal from signal generator 204. Method 2200 optionally further includes step 2206 of generating the first electrical signal and step 2208 of sweeping a frequency of the first electrical signal with respect to a base frequency. Steps 2206 and 2208 are executed in parallel with steps 2202 and 2204. In one example of steps 2206 and 2208, signal generator 204 generates an electrical signal and sweeps a frequency of the electrical signal with respect to a base frequency.

Combinations of Features

Features described above may be combined in various ways without departing from the scope hereof. The following examples illustrate some possible combinations:

(A1) An ultrasound transducer array for coupling sonic energy into a liquid may include a plurality of transducer pairs, where each transducer pair includes an inverted ultrasound transducer and a non-inverted ultrasound transducer electrically coupled in series.

(A2) In the ultrasound transducer array denoted as (A1), the plurality of transducer pairs may be electrically coupled in parallel.

(A3) In any one of the ultrasound transducer arrays denoted as (A1) and (A2), in each of the plurality of transducer pairs, a negative pole of the inverted ultrasound transducer may be electrically coupled with a positive pole of the non-inverted ultrasound transducer.

(A4) In any one of the ultrasound transducer arrays denoted as (A1) and (A2), in each of the plurality of transducer pairs, a positive pole of the inverted ultrasound transducer may be electrically coupled with a negative pole of the non-inverted ultrasound transducer.

(A5) Any one of the ultrasound transducer arrays denoted as (A1) through (A4) may further include a radiating element, and each of the inverted and non-inverted ultrasound transducers of each of the plurality of transducer pairs may be joined to the radiating element.

(A6) In the ultrasound transducer array denoted as (A5), in each of the plurality of transducer pairs, the radiating element may form at least part of an electrical conductor electrically coupling the inverted and non-inverted ultrasound transducers of the transducer pair.

(A7) In any one of the ultrasound transducer arrays denoted as (A5) and (A6), the radiating element may be affixed to a tank for containing a liquid.

(A8) In any one of the ultrasound transducer arrays denoted as (A5) through (A7), the radiating element may be formed of at least one of quartz, sapphire, stainless steel, titanium, tantalum, boron nitride, silicon carbide, silicon nitride, aluminum, and a ceramic material.

(A9) In any one of the ultrasound transducer arrays denoted as (A1) through (A8), in each of the plurality of transducer pairs, the inverted ultrasound transducer may include a piezoelectric element having a positive pole facing a first direction, and the non-inverted ultrasound transducer may include a piezoelectric element having a positive pole facing a second direction that is opposite of the first direction.

(A10) In any one of the ultrasound transducer arrays denoted as (A1) through (A8), in each of the plurality of transducer pairs, the inverted ultrasound transducer may include a Langevin assembly having an inverted configuration, and the non-inverted ultrasound transducer may include a Langevin assembly having a non-inverted configuration.

(A11) In the ultrasound transducer array denoted as (A10), in each of the plurality of transducer pairs, the Langevin assembly having the inverted configuration may include a piezoelectric element having a positive pole facing toward a first direction, and the Langevin assembly having the non-inverted configuration may include a piezoelectric element having a positive pole facing toward a second direction opposite of the first direction.

(A12) In the ultrasound transducer array denoted as (A10), in each of the plurality of transducer pairs: (a) the Langevin assembly having the inverted configuration may include two piezoelectric elements electrically coupled in parallel and having respective positive poles facing towards each other, and (b) the Langevin assembly having the non-inverted configuration may include two piezoelectric elements electrically coupled in parallel and having respective positive poles facing away from each other.

(A13) In the ultrasound transducer array denoted as (A10), in each of the plurality of transducer pairs: (a) the Langevin assembly having the inverted configuration may include two piezoelectric elements electrically coupled in parallel and having respective positive poles facing away from each other, and (b) the Langevin assembly having the non-inverted configuration may include two piezoelectric elements electrically coupled in parallel and having respective positive poles facing towards each other.

(B1) An ultrasound transducer array for coupling sonic energy into a liquid may include a plurality of transducer pairs, where each transducer pair includes an inverted ultrasound transducer and a non-inverted ultrasound transducer electrically coupled in series and configured such that respective piezoelectric elements of the inverted and non-inverted ultrasound transducers expand and contract together when the transducer pair is driven by an electrical signal.

(B2) In the ultrasound transducer array denoted as (B1), the plurality of transducer pairs may be electrically coupled in parallel such that like polarities of piezoelectric elements of the plurality of transducer pairs are connected together.

(B3) Any one of the ultrasound transducer arrays denoted as (B1) and (B2) may further include a radiating element, where the inverted ultrasound transducer and the non-inverted ultrasound transducer of each transducer pair are joined to the radiating element.

(B4) In the ultrasound transducer array denoted as (B3), the radiating element may be affixed to a tank for containing a liquid.

(B5) In any one of the ultrasound transducer arrays denoted as (B3) and (B4), in each of the plurality of transducer pairs, the radiating element may form at least part of an electrical conductor electrically coupling the inverted and non-inverted ultrasound transducers of the transducer pair.

(B6) In any one of the ultrasound transducer arrays denoted as (B1) through (B5), in each of the plurality of transducer pairs, the inverted ultrasound transducer may include a piezoelectric element having a positive pole facing a first direction, and the non-inverted ultrasound transducer may include a piezoelectric element having a positive pole facing a second direction that is opposite of the first direction.

(B7) In any one of the ultrasound transducer arrays denoted as (B1) through (B5), in each of the plurality of transducer pairs, the inverted ultrasound transducer may include a Langevin assembly having an inverted configuration, and the non-inverted ultrasound transducer may include a Langevin assembly having a non-inverted configuration.

(C1) A method for coupling sonic energy into a liquid includes (a) driving a first transducer pair with a first electrical signal, the first transducer pair including a first inverted ultrasound transducer and a first non-inverted ultrasound transducer electrically coupled in series, and (b) driving a second transducer pair with the first electrical signal, the second transducer pair being electrically coupled in parallel with the first transducer pair, and the second transducer pair including a second inverted ultrasound transducer and a second non-inverted ultrasound transducer electrically coupled in series.

(C2) The method denoted as (C1) may further include sweeping a frequency of the first electrical signal with respect to a base frequency.

Changes may be made in the above methods, devices, and systems without departing from the scope hereof. For example, although the ultrasound transducers are discussed above as being either piezoelectric elements or Langevin assemblies, the ultrasound transducers could be other types of ultrasound transducers, including ultrasound transducers without piezoelectric elements, without departing from the scope hereof. It should thus be noted that the matter contained in the above description and shown in the accompanying drawings should be interpreted as illustrative and not in a limiting sense.

What is claimed is:

1. An ultrasound transducer array for coupling sonic energy into a liquid, comprising a plurality of transducer pairs, each transducer pair including an inverted ultrasound transducer and a non-inverted ultrasound transducer electrically coupled in series.

2. The ultrasound transducer array of claim 1, wherein the plurality of transducer pairs are electrically coupled in parallel.

3. The ultrasound transducer array of claim 2, wherein in each of the plurality of transducer pairs, a negative pole of the inverted ultrasound transducer is electrically coupled with a positive pole of the non-inverted ultrasound transducer.

4. The ultrasound transducer array of claim 2, wherein in each of the plurality of transducer pairs, a positive pole of the inverted ultrasound transducer is electrically coupled with a negative pole of the non-inverted ultrasound transducer.

5. The ultrasound transducer array of claim 2, further comprising a radiating element, wherein the inverted and non-inverted ultrasound transducers of each of the plurality of transducer pairs are joined to the radiating element.

6. The ultrasound transducer array of claim 5, wherein in each of the plurality of transducer pairs, the radiating element forms at least part of an electrical conductor electrically coupling the inverted and non-inverted ultrasound transducers of the transducer pair.

7. The ultrasound transducer array of claim 5, wherein the radiating element is affixed to a tank for containing a liquid.

8. The ultrasound transducer array of claim 5, wherein the radiating element is formed of at least one of quartz, sapphire, stainless steel, titanium, tantalum, boron nitride, silicon carbide, silicon nitride, aluminum, and a ceramic material.

9. The ultrasound transducer array of claim 5, wherein in each of the plurality of transducer pairs, the inverted ultrasound transducer includes a piezoelectric element having a positive pole facing a first direction, and the non-inverted ultrasound transducer includes a piezoelectric element having a positive pole facing a second direction that is opposite of the first direction.

10. The ultrasound transducer array of claim 5, wherein in each of the plurality of transducer pairs, the inverted ultrasound transducer includes a Langevin assembly having an inverted configuration, and the non-inverted ultrasound transducer includes a Langevin assembly having a non-inverted configuration.

11. The ultrasound transducer array of claim 10, wherein in each of the plurality of transducer pairs, the Langevin assembly having the inverted configuration includes a piezoelectric element having a positive pole facing toward a first direction, and the Langevin assembly having the non-inverted configuration includes a piezoelectric element having a positive pole facing toward a second direction opposite of the first direction.

12. The ultrasound transducer array of claim 10, wherein in each of the plurality of transducer pairs: (a) the Langevin assembly having the inverted configuration includes two piezoelectric elements electrically coupled in parallel and having respective positive poles facing towards each other, and (b) the Langevin assembly having the non-inverted configuration includes two piezoelectric elements electrically coupled in parallel and having respective positive poles facing away from each other.

13. The ultrasound transducer array of claim 10, wherein in each of the plurality of transducer pairs: (a) the Langevin assembly having the inverted configuration includes two piezoelectric elements electrically coupled in parallel and having respective positive poles facing away from each other, and (b) the Langevin assembly having the non-inverted configuration includes two piezoelectric elements electrically coupled in parallel and having respective positive poles facing towards each other.

14. An ultrasound transducer array for coupling sonic energy into a liquid, comprising a plurality of transducer pairs, each transducer pair including an inverted ultrasound transducer and a non-inverted ultrasound transducer electrically coupled in series and configured such that respective piezoelectric elements of the inverted and non-inverted ultrasound transducers expand and contract together when the transducer pair is driven by an electrical signal.

15. The ultrasound transducer array of claim 14, wherein the plurality of transducer pairs are electrically coupled in parallel such that like polarities of piezoelectric elements of the plurality of transducer pairs are connected together.

16. The ultrasound transducer array of claim 15, further comprising a radiating element, wherein the inverted ultrasound transducer and the non-inverted ultrasound transducer of each transducer pair are joined to the radiating element.

17. The ultrasound transducer array of claim 16, wherein the radiating element is affixed to a tank for containing a liquid.

18. The ultrasound transducer array of claim 16, wherein in each of the plurality of transducer pairs, the radiating element forms at least part of an electrical conductor electrically coupling the inverted and non-inverted ultrasound transducers of the transducer pair.

19. The ultrasound transducer array of claim 15, wherein in each of the plurality of transducer pairs, the inverted ultrasound transducer includes a piezoelectric element having a positive pole facing a first direction, and the non-inverted ultrasound transducer includes a piezoelectric element having a positive pole facing a second direction that is opposite of the first direction.

20. The ultrasound transducer array of claim 15, wherein in each of the plurality of transducer pairs, the inverted ultrasound transducer includes a Langevin assembly having an inverted configuration, and the non-inverted ultrasound transducer includes a Langevin assembly having a non-inverted configuration.

* * * * *